United States Patent

Larson et al.

Patent Number: 5,021,511
Date of Patent: Jun. 4, 1991

[54] POLYMER COMPOSITIONS DERIVED FROM ACRYLOXYALKYLCYANOACETAMIDES

[75] Inventors: Gary R. Larson, Hatfield; William D. Emmons, Huntingdon Valley, both of Pa.; Palaiyur S. Kalyanaraman, Fanwood, N.J.

[73] Assignee: Rohm and Haas Company, Philadelphia, Pa.

[21] Appl. No.: 290,672

[22] Filed: Dec. 27, 1988

[51] Int. Cl.$^5$ .............................................. C08F 20/60
[52] U.S. Cl. ................................... 525/295; 526/298
[58] Field of Search ....................... 526/298; 525/295

[56] References Cited

U.S. PATENT DOCUMENTS

| | | | |
|---|---|---|---|
| 2,439,081 | 4/1948 | Dickey et al. | 526/298 |
| 2,669,558 | 2/1954 | Mowry et al. | 526/298 |
| 2,720,512 | 10/1955 | Butler | 526/298 |
| 2,723,260 | 11/1955 | Mowry et al. | 526/298 |
| 2,833,751 | 5/1958 | Luskin et al. | 526/298 |
| 2,834,765 | 5/1958 | DeBenneville | 526/298 |
| 2,850,486 | 9/1958 | D'Alelio | 526/298 |
| 3,338,954 | 8/1967 | McFadden et al. | 526/298 |
| 4,217,439 | 8/1980 | Heckles | 528/228 |
| 4,229,505 | 10/1980 | Heckles | 528/228 |
| 4,247,673 | 1/1981 | Ponticello et al. | 526/263 |
| 4,408,018 | 10/1983 | Bartman et al. | 525/300 |
| 4,611,041 | 9/1986 | Stockinger et al. | 526/298 |

*Primary Examiner*—Joseph L. Schofer
*Assistant Examiner*—N. Sarofim

[57] ABSTRACT

Novel polymers are prepared from at least one cyanoacetamide monomer having the formula:

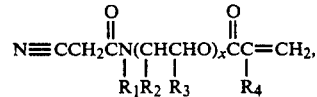

where $R_1$ is —$CH_3$, —$(CH_2)_mCH_3$ or —H; $R_2$ and $R_3$ independently are —H, ($C_1$-$C_4$) alkyl or aryl; $R_4$ is —$CH_3$, —$(CH_2)_nCH_3$ or —H; m is 1 to 10; n is 1 to 10; and x is 1 to 20.

These polymers can be readily reacted by a carbon-Michael addition reaction with carbon-Michael acceptors, such as polyfunctional acrylates, methacrylates, fumarates, maleates and aopates to form crosslinked polymer compositions.

7 Claims, No Drawings

POLYMER COMPOSITIONS DERIVED FROM ACRYLOXYALKYLCYANOACETAMIDES

SUMMARY OF THE INVENTION

This invention relates to novel polymers which are prepared from at least one monomer having the chemical formula:

where $R_1$ is $-CH_3$, $-(CH_2)_m CH_3$ or $-H$; $R_2$ and $R_3$ independently are $-H$, $(C_1-C_4)$ alkyl or aryl; $R_4$ is $-CH_3$, $-(CH_2)_n CH_3$ or $-H$; m is 1 to 10; n is 1 to 10; and x is 1 to 20.

The novel polymers of this invention can be easily reacted by a carbon-Michael addition reaction with carbon-Michael acceptors, such as polyfunctional acrylates, methacrylates, maleates, fumarates and aopates to form crosslinked polymer composition. These polymers are useful in a variety of coatings, adhesives, caulks, mastics, and cement applications. The polymers exhibit faster rates of cures, curing and crosslinking at ambient temperatures, improved physical properties such as hardness and weatherability, and improved hydrolysis resistance.

BACKGROUND OF THE INVENTION

Ambient-cure compositions based on carbon-Michael reaction between active methylene groups and active alkene groups are known in the art. U.S. Pat. Nos. 4,217,396; 4,217,439; 4,218,515 and 4,229,505 disclose crosslinked polymers from polyfunctional acrylates, cyanoacetates, diacetoacetamides, and ureadiacetoacetamides. The crosslinking is activated by strongly basic catalysts such as sodium methoxide, sodium metal, sodium ethylate and benzyl-trimethyl ammonium methoxide.

U.S. Pat. No. 4,408,018 teaches the use of base catalysts to activate carbon-Michael cure reactions of mixtures of acetoacetate polymers and polyfunctional acrylates. Other related inventions involve carbon-Michael reactions with acetoacetate polymers as carbon-Michael donors and maleate polyesters and fumarate polyesters as carbon-Michael acceptors.

U.S. Pat. No. 3,658,878 discloses the use of active-methylene containing polymers as hardening agents in photographic applications. The '878 patent specifically discloses polymers made from acetoacetate and cyanoacetate (ester) monomers.

U.S. Pat. No. 4,247,673 discloses crosslinkable polymers derived from various amides and which are useful in photographic applications.

Some disadvantages with the prior are compositions involving carbon-Michael curing reactions are the relatively slow cure rates, susceptibility to hydrolysis, and relative nonreactivity with poly (methacrylate) crosslinkers. The present invention effectively overcomes these disadvantages by providing polymers polymerized from cyanoacetamide monomers which are readily crosslinked by carbon-Michael reactions with a variety of carbon-Michael acceptors.

It is an object of the present invention to provide novel polymer compositions which cure relatively rapidly at ambient temperatures. It is a further object of this invention to provide polymer compositions which have improved hydrolysis resistance, hardness and weatherability. If is an even further object of this invention to provide novel polymers which can be rapidly crosslinked by polyfunctional methacrylates to yield polymer compositions which are relatively non-toxic in comparison to prior art compositions.

DETAILED DESCRIPTION

Applicants have discovered that novel polymers which are prepared from at least one cyanoacetamide monomer can be rapidly crosslinked by carbon-Michael addition reaction with a variety of carbon-Michael acceptors. These polymers can find utility in diverse applications such as coatings, adhesives, caulks, mastics, and cement modifiers.

The cyanoacetamide monomers which are useful in this invention can be represented by the chemical formula:

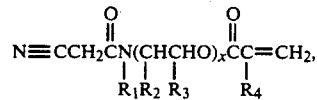

where $R_1$ is $-CH_3$, $-(CH_2)_m CH_3$ or $-H$; $R_2$ and $R_3$ independently are $-H$, $(C_1-C_4)$ alkyl or aryl; $R_4$ is $-CH_3$, $-(CH_2)_n CH_3$ or $-H$; m is 1 to 10; n is 1 to 10; and x is 1 to 20. Preferably $R_1$ and $R_4$ are $-CH_3$, $R_2$ and $R_3$ are $-H$, and x is 1. This preferred monomer is identified as N-cyanoacetyl-N-methylaminoethyl methacrylate ("CMAEMA").

The cyanoacetamide monomers useful in the present invention can be prepared by a 2-step process involving (1) reacting the appropriate 2-(alkylamino) alcohol with the appropriate alkyl-cyanoacetate and (2) subsequently reacting this intermediate with an alkyl methacrylate. A suitable catalyst can be used in step (2) such as dibutyltin oxide, to catalyze the transesterification of the alkyl methacrylate.

The novel polymers of this invention can be prepared by conventional polymerization processes which are known in the art. Preferably the polymers are prepared by solution polymerization in an organic solvent, such as, for example, methyl ethyl ketone, xylene or the like. The novel polymers of this invention can comprise by weight from about 1% to 100% of the cyanoacetamide monomers of the prescribed formula. Preferably the polymers comprise from about 10% to about 100% by weight of said cyanoacetamide monomer or mixtures thereof. Applicants surprisingly discovered that, in addition to the free-radical copolymerizion with ethylenically-unsaturated monomers, these cyanoacetamide monomers can rapidly homopolymerize by carbon-Michael addition reaction when catalyzed with base.

The ethylenically-unsaturated monomers which can be copolymerized by free-radical polymerization with the cyanoacetamide monomers to form the novel polymers of this invention can be any monomer containing the vinylic group $>C=C<$. Examples of suitable co-monomers include vinyl esters such as vinyl acetate, vinyl butyrate and the like; vinyl amides such as acrylamide, methacrylamide, N-methyl-acrylamide and the like; vinyl nitriles such as acrylonitrile, methacrylonitrile, 3-butenenitrile and the like; vinyl ketones such as methyl vinyl ketone, diacetone acrylamide and the like;

vinyl halides such as vinyl chloride, vinyl bromide, vinylidene chloride and the like; vinyl ethers such as vinyl methyl ether, vinyl phenyl ether and the like; alpha-beta-unsaturated acids and esters thereof such as acrylic acid, methacrylic acid, itaconic acid, maleic acid, fumaric acid, methyl methacrylate, butyl acrylate, 2-ethylhexyl acrylate, 2-hydroxyethyl methacrylate, dimethyl itaconate, dimethyl maleate, dimethyl fumarate, and the like; olefins such as ethylene, propylene, butadiene, isoprene and the like; and vinyl aromatics such as styrene, alpha-methylstyrene, p-chlorostyrene and the like.

The weight average molecular weight of the novel polymers of this invention is not critical and can range from about 1,000 to about 1,000,000; preferably about 10,000 to about 100,000.

The novel polymers of this invention can be crosslinked with a wide range of carbon-Michael acceptors by a carbon-Michael addition reaction. Preferred compounds which function as carbon-Michael acceptors for use in this invention are the polyfunctional acrylates, polyfunctional methacrylates, polyfunctional maleates, polyfunctional fumarates and polyfunctional acryloxypropanoates. Examples of suitable carbon-Michael acceptor compounds include: trimethylol propane tri(acryloxypropanoate), ethylene glycol diacrylate, 1,4-butanediol diacrylate, bisphenol A diacrylate, diethylene glycol diacrylate, pentaerythritol triacrylate, pentaerythritol tetraacrylate, trimethylolpropane triacrylate, polyethylene glycol diacrylate, bisphenol A diglycidal ether diacrylate, ethoxylated bisphenol A diacrylate, hexanediol diacrylate, tripropyleneglycol diacrylate, 1,4-cyclohexane dimethanol diacrylate and the corresponding methacrylate analogs such as trimethylol propane trimethacrylate. Other suitable carbon-Michael acceptors are the unsaturated polyesters such as for example, fumarate polyesters, maleate polyesters, and the like. The most preferred carbon-Michael acceptors are the polyfunctional methacrylates.

The crosslinked polymeric compositions of this invention are prepared by mixing the novel polymer with the carbon-Michael acceptor compounds over a wide range of ratios. It is preferred that the novel polymer and carbon-Michael acceptor be mixed to give about 0.5 to about 3 alkene groups per active methylene group. Suitable catalyst for the carbon-Michael crosslinking reaction can be any basic catalyst, such as, for example, potassium hydroxide, sodium hydroxide, potassium amylate, potassium ethoxide, sodium methoxide, sodium metal, sodium ethylate, sodium bicarbonate, benzyl-trimethyl ammonium methoxide, quaternary ammonium bases (such as tetrabutyl ammonium hydroxide) and the like. The reaction can proceed without catalyst or an effective amount of basic catalyst may be used, generally in the range of about 10 millimoles of catalyst per 100 grams of polymer composition. Further information on carbon-Michael reactions can be found in "The Michael Reaction" by E. D. Bergmann et al, *Organic Reactions*, Vol. 10, pages 179–555 and *Modern Synthetic Reactions*, H. O. House, 2nd Edition (1972), pages 595–623.

After mixing the components to form the polymeric compositions of this invention, said compositions can be used in their present form or blended with other conventional additives such as pigments, fillers, dispersants, wetting agents, coalescents, rheology modifiers, biocides, stabilizers and the like. The polymer compositions of this invention exhibit faster rates of cures, curing and crosslinking at ambient temperatures, improved physical properties such as hardness and weatherability and improved hydrolysis resistance.

The following examples are presented to demonstrate this invention. The examples are intended to be illustrative and not limitative. All parts and percentages used in the examples are on a weight basis unless otherwise indicated.

| | |
|---|---|
| CMAEMA = | N-cyanoacetyl-N-methylaminoethyl methacrylate |
| MMA = | methyl methacrylate |
| STY = | styrene |
| BMA = | butyl methacrylate |
| BA = | butyl acrylate |
| AN = | acrylonitrile |
| i-BMA = | iso-butyl methacrylate |
| GMA = | glycidyl methacrylate |
| DMAPMA = | dimethylaminopropylmethacrylate |
| DMAEMA = | dimethylaminoethylmethacrylate |
| TMPMA = | trimethylolpropane trimethacylate |
| DEF = | diethyl fumarate |
| AAEM = | acetoacetoxyethyl methacrylate |
| MAK = | methyl amyl ketone |
| MEK = | methyl ethyl ketone |
| TBPO = | t-butyl peroctoate |
| L-10M = | t-butyl peroxyneodecanoate |
| MEHQ = | methyl ether of hydroquinone |
| TBAH = | tetrabutylammonium hydroxide (25 wt. % in methanol) |
| TBAB = | tetrabutylammonium bicarbonate (19 wt. % in methanol) |

EXAMPLE I

A three-necked 2,000 ml. flask equipped with a thermometer, a mechanical stirrer, a nitrogen sparge tube, a condenser and a 300 ml. pressure-equalizing additional funnel, was charged with 594.5 g. of methyl cyanoacetate. 2-(methylamino) ethanol (366.5 g.) was added at a rate of 14 ml./min under a nitrogen atmosphere. The temperature of the reaction mixture slowly rose to 65 degrees C. After the addition of 2-(methylamino) ethanol was completed, the reaction mixture was stirred for one hour without external cooling. The reaction mixture was subsequently heated to 30°-40° C. under vacuum for one hour. The resulting intermediate product was identified by NMR and Infrared spectroscopy as N-(2-hydroxyethyl) -N-methyl-2-cyanoacetamide.

A 1,000 ml. four-necked flask equipped with a thermometer, air sparge tube, magnetic stirrer and a perforated plate distilling column with an adjustable take off distillation head attached, was charged with 71.18 g of the N-(2-hydroxyethyl)-N-methyl 2-cyanoacetamide, 110.13 g of methyl methacrylate and 0.084 g of MEHQ. The mixture was dried by the azeotropic distillation of the water. After cooling the reaction mixture to 70 degrees C., 1.24 g of dibutyltin oxide was charged to the flask. The mixture was again heated under reflux and the methanol methyl methacrylate azeotrope was collected when the temperature at the distillation head dropped below 69 degrees C. After three hours, the temperature remained at 70 degrees C. without any further removal of the azeotropic mixture. The reaction mixture was concentrated under vacuum to remove the excess methyl methacrylate. Upon concentration 210 grams of a brown oil was obtained. The final product was identified as N-cyanoacetyl-N-methylaminoethyl methacrylate by NMR and Infrared Spectroscopy.

EXAMPLE II

A 1-liter, 4-necked flask, equipped with a thermometer, mechanical stirrer, heating mantle and 2 fluid-metering pumps, was charged with 1021 grams of methyl amyl ketone and heated to 105° C. A monomer mix consisting of 60.63 grams of CMAEMA, 116.5 grams of MMA, 59.05 grams of BMA and 59.05 grams of STY was added to the flask at a rate of 5.5 ml./minute. A catalyst solution consisting of 13.3 grams of t-butyl peroctoate and 95 grams of methyl amyl ketone was added concurrently with the monomer mix at a rate of 2.2 ml./minute. After the monomer mix and catalyst feeds were complete, the reaction mixture was maintained at 80° C. for 20 minutes. A chaser consisting of 1 gram of t-butyl peroctoate was then added, followed by a similar chaser 5 minutes later. The reaction mixture was maintained at 105° C. for 15 minutes and then cooled to room temperature. The resulting polymer product had the following characteristics: 60.2% solids; 1470 centipoise Brookfield viscosity; 29,300 wt. avg. mol. wt.; 9830 no. avg. mol. wt.

moles diethyl fumarate and 4 moles 2-methyl-2-propyl-1, 3, propanediol) at a ratio of 1.5 alkene units of the polyester per active methylene unit of the polymers. Catalyst was used at a level of 10 millimoles per 100 grams of the composition. After the above components were mixed together, a 4-mil wet film was cast on (Bonderite 1000) steel panels and cured at ambient room temperature. The crosslinking time of each film was measured by determining the time required for each film to become insoluble in methylene dichloride. The results are presented in Table II.

TABLE 1

| EX. | POLYMER COMPOSITION (wt. %) | SOLVENT | CATALYST | % SOLIDS | (centipoise) VISCOSITY | MW | MN |
| --- | --- | --- | --- | --- | --- | --- | --- |
| III | 50 MMA/20 BA/20 STY/10 CMAEMA | XYLENE | TBPO | 58.6 | 18,600 | 34,200 | 6,850 |
| IV | 40 MMA/20 BA/20 STY/20 CMAEMA | XYLENE | TBPO | 49.6 | 400 | 26,200 | 9,200 |
| V | 50 MMA/20 BA/20 STY/10 CMAEMA | MAK | L-10M | 58.2 | 4,400 | 21,600 | 7,120 |
| VI | 40 MMA/20 BA/20 STY/20 CMAEMA | MAK | L-10M | 60.2 | 1,470 | 29,300 | 9,830 |
| VII | 30 MMA/20 BA/20 STY/30 CMAEMA | MEK | L-10M | 60.4 | 1,240 | 31,300 | 9,390 |
| VIII | 20 MMA/20 BA/20 STY/40 CMMAEMA | MEK | L-10M | 62.5 | 8,040 | 78,300 | 18,600 |
| IX | 15 MMA/20 BA/20 STY/5 DMAPMA/ 40 CMAEMA | MEK | L-10M | 62.5 | 2,540 | 29,700 | 9,800 |
| X | 92.5 BA/2.5 AN/5 CMAEMA | XYLENE | TBPO | 80.3 | 5,550 | 51,300 | 9,090 |
| XI | 20 BMA/15 STY/15 MMA/40 CMAEMA | MEK | L-10M | 61.4 | 29,900 | 16,400 | 3,130 |
| XII | 50 i-BMA/10 DMAEMA/40 CMAEMA | MEK | L-10M | 59.8 | 4,000 | 26,500 | 7,400 |
| XIII | 20 BMA/20 GMA/10 STY/ 40 CMAEMA | MEK | L-10M | 62.7 | 10,850 | 73,000 | 14,600 |
| XIV | 40 i-BMA/20 GMA/40 CMAEMA | MEK | L-10M | 58.1 | 1,430 | 43,100 | 10,900 |

MW = wt. avg. molecular weight
MN = no. avg. molecular weight

TABLE II

| POLYMER | CATALYST | % TOTAL SOLIDS | CROSSLINKING TIME |
| --- | --- | --- | --- |
| EX. V | TBAH | 51.4 | <1 minute* |
| EX. V | TBAB | 51.4 | <43 minutes |
| EX. VI | TBAB | 52.2 | <31 minutes |

*Gelled while mixing, indicating immediate crosslinking

EXAMPLE III-XIV

Various polymers within the scope of this invention were prepared following the procedures of Ex. II. The respective monomers, solvent and catalyst were used as shown in Table I.

EXAMPLE XV

A homopolymer of CMAEMA was prepared by mixing 2.1 grams of CMAEMA monomer with 0.5 grams of tetramethylguanidine catalyst at room temperature by carbon-Michael addition reaction. The reaction mixture became very warm and gelled after 15 minutes. The resulting gel was found to be soluble in methylene chloride solvent, indicating a polymer with no crosslinking.

EXAMPLE XVI

Polymers within the scope of the present invention were mixed with fumarate polyester (composed of 5

EXAMPLES XVII-XVIII

For comparative purposes, acetoacetate polymers falling outside the scope of this invention were prepared as described in U.S. Pat. No. 4,408,018. These polymers had the following composition.
Ex. XVII: 50 MMA/20 BMA/20 STY/10 AAEM (60.4% solids in MAK)
Ex. XVIII: 40 MMA/20 BMA/20 STY/20 AAEM (60.1% solids in MAK)

EXAMPLE XIX

Polymers within the scope of this invention prepared in Ex. V and Ex. VI respectively were mixed with a polyfunctional methacrylate (TMPMA) at a ratio of 1.5 alkene units of the TMPMA per active methylene unit. Catalyst was added to the mixture at a level of 10 millimoles of catalyst per 100 grams of the mixture. 4-mil wet films were cast on (Bonderite 1000) steel panel and cured at ambient room temperature. The crosslinking time of each film was measured by determining the time required for the film to become insoluble in methylene dichloride. For comparative purposes, compositions were prepared as above using the acetoacetate polymers from Ex. XVII and Ex. XVIII and measured for crosslinking time. The results are presented in Table III and demonstrate that the polymers of this invention react with polyfunctional methacrylates at surprisingly faster rates that the acetoacetate polymers of the prior art.

TABLE III

| POLYMER | CATALYST | % TOTAL SOLIDS | CROSSLINKING TIME |
|---|---|---|---|
| EX. V | TBAH | 51.07 | 6-7 hours |
| EX. V | TBAB | 51.07 | 6-7 hours |
| EX. VI | TBAH | 52.12 | 1.5-2.0 hours |
| EX. VI | TBAB | 52.12 | 1.0-1.5 hours |
| EX. XVII (comparative) | TBAH | 51.07 | >24 hours |
| EX. XVII (comparative) | TBAB | 51.07 | >24 hours |
| EX. XVIII (comparative) | TBAH | 52.12 | >24 hours |
| EX. XVIII (comparative) | TBAB | 52.12 | >24 hours |

EXAMPLES XX-XXI

Following the procedures of Ex. II, a polymer within the scope of this invention was prepared having a composition of 40 CMAEMA/20 BMA/20 STY/15 MMA/5 DMAPMA. For comparative purposes an acetoacetate polymer was prepared having a composition of 40 AAEM/20 BMA/20 STY/15 MMA/5 DMAPMA. The polymers were formulated into a blue paint using fumarate polyester (as described in Ex. XVI) as the crosslinker and epoxy and tetrabutylammonium hydroxide as the catalyst. Films of the paints were prepared and subjected to ultraviolet radiation for 1000 hours. The films were evaluated for weatherability by measuring the % retention of initial gloss. The results are presented below and demonstrate that the composition of this invention (Ex. XX) has improved weatherability compared to the acetoacetate composition (Ex. XXI).

| Sample | Polymer Composition | Gloss Retention (%) |
|---|---|---|
| Ex. XX | 40 CMAEMA/20 BMA/20 STY/15 MMA/5 DMAPMA | 66 |
| Ex. XXI (comparative) | 40 AAEM/20 BMA/20 STY/15 MMA/5 DMAPMA | 32 |

EXAMPLE XXII-XXIII

Following the procedures of Ex. XX, a paint formulation was prepared except that trimethylolpropane tri(acryloxypropanoate) was used as the crosslinker. Following the procedures of Ex. XXI, a comparative paint formulation was prepared except that trimethylolpropane tri(acryloxypropanoate) was used as the crosslinker. Films were prepared, subjected to ultraviolet radiation for 800 hours, and evaluated for weatherability by measuring gloss retention. The results are presented below:

| Sample | Polymer Composition | Gloss Retention (%) |
|---|---|---|
| EX. XXII | 40 CMAEMA/20 BMA/10 STY 15 MMA/5 DMAPMA | 49 |
| EX. XXIII (comparative) | 40 AAEM/20 BMA/20 STY 15 MMA/5 DMAPMA | 12 |

EXAMPLE XXIV-XXV

A polymer composition (Ex. XXIV) within the scope of this invention was prepared following the procedures of Ex. II having the following composition:
40 CMAEMA/20MMA/20BMA/20 STY A polymer composition (Ex. XXV) falling outside the scope of this invention was prepared following the procedures of Ex. XVII having the following composition:
40AAEM/20MMA/20BMA/20STY Each of these polymer compositions was mixed with trimethylolpropane triacryloxypropanoate at a ratio of 1 alkene unit per active methylene unit. TBAB catalyst was added at a level of 10 millimoles per 100 grams of the composition. The samples were cast into films following the procedures of Ex. XIX. The films were cured at ambient room temperature for 1, 3, 7 and 14-day periods and evaluated for hardness using a Tukon Hardness Tester. The results are presented in Table IV, and demonstrate that the polymer compositions of this invention have improved hardness over acetoacetate polymer compositions of the prior art.

TABLE IV

| Sample | Knoop Hardness | | | |
|---|---|---|---|---|
| | 1 day | 3 days | 7 days | 14 days |
| Ex. XXIV | 3.81 | 7.17 | >11.0 | >11.0 |
| Ex. XXV (comparative) | 1.20 | 1.56 | 2.45 | 10.43 |

We claim:

1. A composition of matter comprising a polymer which is prepared from at least one cyanoacetamide monomer having the formula:

where $R_1$ is —$CH_3$, —$(CH_2)_M CH_3$ or —H; $R_2$ and $R_3$ independently are —H, ($C_1$-$C_4$) alkyl or aryl; $R_4$ is —$CH_3$ —$(CH_2)_n CH_3$ or H; m is 1 to 10; n is 1 to 10; and x is 1 to 20; wherein said polymer is reacted with one or more compound(s) functioning as a carbon-Michael acceptor to form a carbon-Michael reaction product.

2. A composition of claim 1 wherein said compound(s) functioning as a carbon-Michael acceptor are selected from the group consisting of polyfunctional acrylates, polyfunctional methacrylates, polyfunctional maleates, polyfunctional fumarates and polyfunctional acryloxypropanoates.

3. A composition of claim 2 wherein said carbon-Michael acceptor is trimethylolpropanetrimethacrylate.

4. A composition of claim 2 wherein said carbon-Michael acceptor is a fumarate polyester.

5. A composition of claim 2 wherein said carbon-Michael acceptor is trimethylolpropane tri(acryloxypropanoate).

6. A composition of claim 2 wherein said carbon-Michael acceptor is trimethylolpropane triacrylate.

7. A crosslinked polymeric composition comprising the carbon-Michael addition reaction product of (a) a polymer prepared from at least one cyanoacetamide monomer having the formula:

where $R_1$ is $-CH_3$, $-(CH_2)_m CH_3$ or $-H$; $R_2$ and $R_3$ independently are $-H$, $(C_1-C_4)$ alkyl or aryl; $R_4$ is $-CH_3$, $-(CH_2)_n CH_3$ or $-H$; m is 1 to 10; n is 1 to 10; x is 1 to 20 and (b) one or more compounds functioning as a carbon-Michael acceptor selected from the group consisting of polyfunctional acrylates, polyfunctional methacrylates, polyfunctional maleates, polyfunctional fumarates and polyfunctional acryloxypropanoates.

* * * * *